United States Patent [19]

Zalessky et al.

[11] 4,240,292

[45] Dec. 23, 1980

[54] METHOD FOR TRIGGERING ULTRASONIC FLOW METER AND ULTRASONIC FLOW METER ADAPTED FOR SAME

[76] Inventors: Eduard A. Zalessky, ulitsa Tashkentskaya, 130, kv.11; Vladimir V. Smyshlyaev, ulitsa Michurina, 116, kv. 57, both of Kuibyshev, U.S.S.R.

[21] Appl. No.: 16,339

[22] Filed: Feb. 28, 1979

[30] Foreign Application Priority Data

Mar. 3, 1978 [SU] U.S.S.R. .............................. 2585951

[51] Int. Cl.³ ............................................... G01F 1/66
[52] U.S. Cl. ..................................... 73/861.27; 73/579
[58] Field of Search ............................. 73/194 A, 597

[56] References Cited

U.S. PATENT DOCUMENTS

| 3,715,709 | 2/1973 | Zacharias, Jr. et al. | 73/194 A X |
| 4,095,457 | 6/1978 | Koda et al. | 73/597 X |
| 4,144,753 | 3/1979 | Larsen | 73/194 A |

Primary Examiner—Charles A. Ruehl
Attorney, Agent, or Firm—Steinberg & Raskin

[57] ABSTRACT

A method for triggering an ultrasonic flow meter comprising a synchronized ring circuit, consists of periodically turning the ring circuit on and off by trigger pulses whose repetition period is varied within the range of possible changes of the repetition period of autocirculation pulses of the synchronized ring circuit until an autocirculation pulse is matched with a trigger pulse. At such point, the application of trigger pulses to the synchronized ring circuit is discontinued by matching the frequency of the trigger pulses with that of the autocirculation pulses via continuous automatic phase control of the trigger pulse frequency. With no autocirculation pulses in the synchronized ring circuit, the application of trigger pulses is resumed.

9 Claims, 14 Drawing Figures

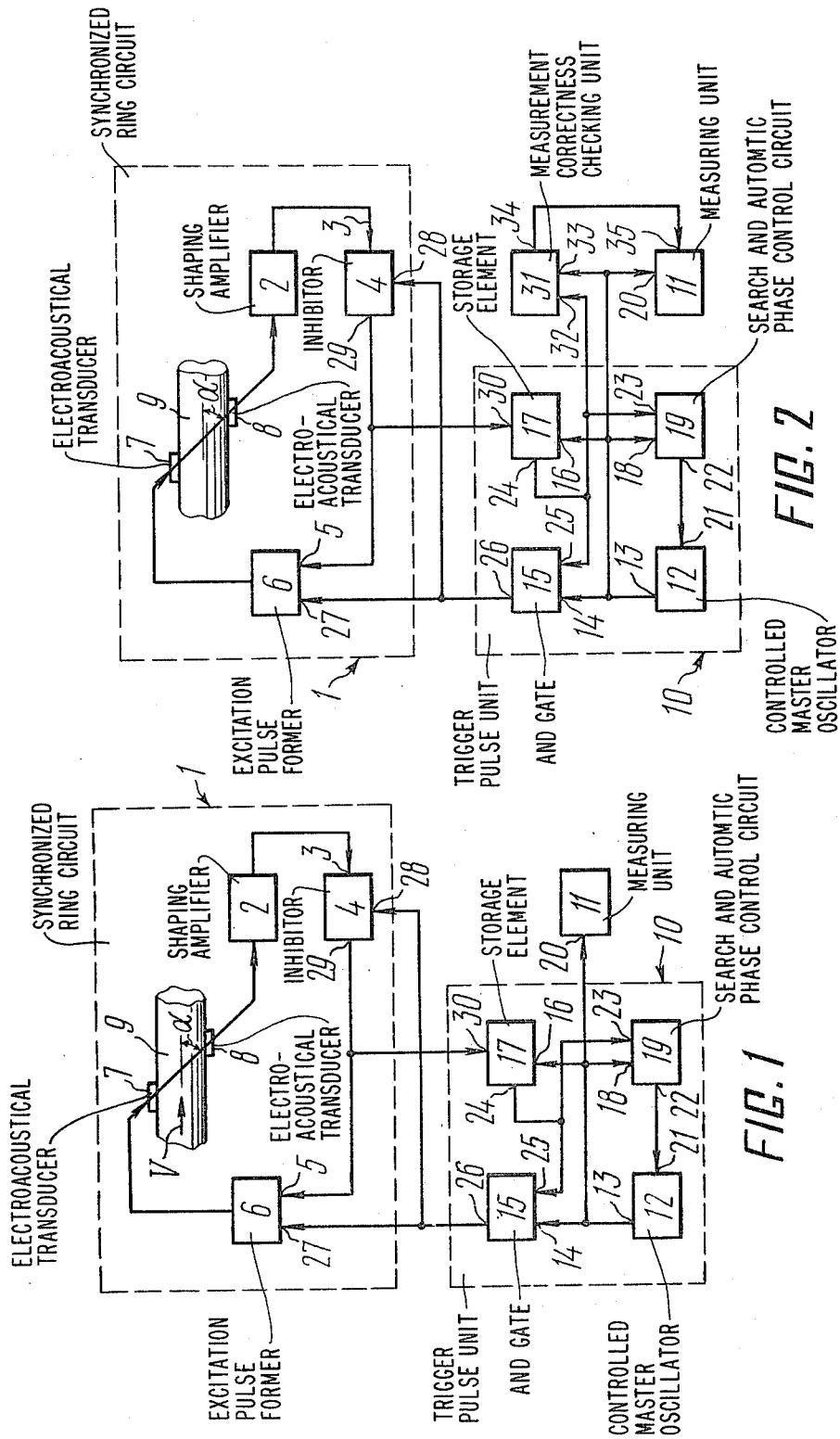

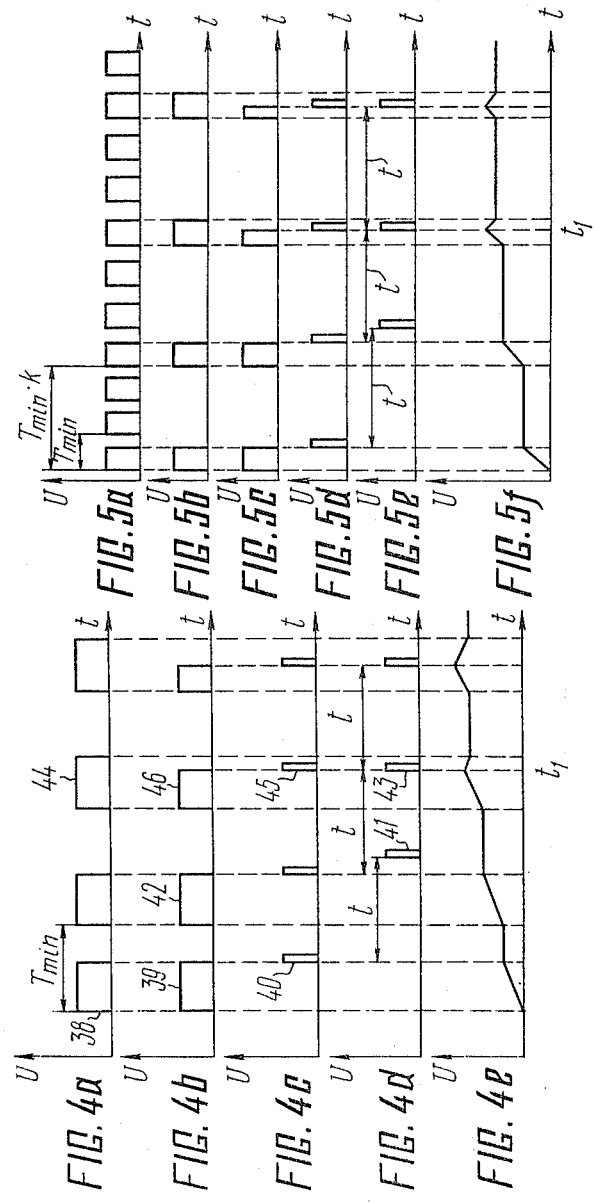

METHOD FOR TRIGGERING ULTRASONIC FLOW METER AND ULTRASONIC FLOW METER ADAPTED FOR SAME

FIELD OF THE INVENTION

The present invention relates to ultrasonic measurements and, more specifically, to a method for triggering an ultrasonic flow meter and an ultrasonic flow meter adapted for that method.

The invention is applicable to pulse-frequency ultrasonic flow meters intended to automatically monitor the flow rate of oil and chemical products, liquid foodstuffs, water, etc.

BACKGROUND OF THE INVENTION

In this specification, the term "flow meter" refers to a flow velocity and flow rate measuring instrument, keeping in mind that in the case of measurements based on the propagation of acoustical waves flow rate is a function of flow velocity.

The growing need for highly accurate measurements of flow rates of all kinds of fluids, including petroleum products, accounts for increasingly stringent requirements imposed today on pulse-frequency ultrasonic flow rate measuring techniques carried out with the aid of ultrasonic flow meters of the type that comprises a synchronized ring circuit, i.e. a pulse generating system with a delayed acoustic feedback. Flow meters of this type are accurate only if the triggering results in a continuous autocirculation of a pulse through the synchronized ring circuit. This statement applies only to the pulse that carries useful information. In actual measuring systems, however, the acoustical channel, i.e. the spacing intended for passage of a medium to undergo flow rate measurements and found between two electroacoustical transducers, is subject to periodic disturbances which affect the accuracy of measurements and are due to the scattering of the ultrasonic beam by gas bubbles and foreign particles contained in the medium. With the flow, foreign particles drawn away by the flow, one must restore the operating state of the flow meter, i.e. the continuous autocirculation of a pulse through the synchronizing ring circuit. A delayed triggering of the flow meter or an autocirculation of two or more pulses through the ring circuit distort the results of the measurements.

There is known a method for triggering a pulse-frequency ultrasonic flow meter, consisting of simultaneously turning on the synchronizing ring circuit and applying a trigger pulse thereto.

There is known an ultrasonic flow meter adapted for this method and comprising two synchronized ring circuits, each incorporating, in a series arrangement, an amplifier, an excitation pulse former and two electroacoustical transducers separated by a gap intended for passage of a medium to be subjected to flow rate measurements. The electroacoustical transducers are so oriented in relation to each other that one of them can transmit and the other receive an acoustical signal traveling at an angle $\alpha$ other than 90° to the flow direction. The flow meter under consideration further includes an auxiliary oscillator and a measuring unit which are both connected to the synchronized ring circuits.

In each synchronized ring circuit of such a flow meter, the oscillator transmits a pulse to the excitation pulse former whose output signal is applied to that electroacoustical transducer which sends a pulse into the medium. This pulse is received by the second electroacoustical transducer and again applied to the excitation pulse former, whereby an autocirculation of pulses in the synchronized ring circuit is effected. The difference $\Delta f$ of the frequencies at which the autocirculation of pulses takes place in the synchronized ring circuits is indicative of the flow velocity V.

For example, with two electroacoustical transducers arranged on the opposite sides of a pipeline whose diameter is D, $$\Delta f = \sin 2\alpha / D \cdot V \tag{1}$$

However, the method under review does not provide for an automatic retriggering of the flow meter following a temporary disturbance in the acoustic channel, because it does not include the operation of resuming the autocirculation of a pulse through the synchronized ring circuit. The autocirculation indicates that the flow meter is in good working order and unless it takes place, one must bring into play and auxiliary oscillator so as to apply a trigger pulse to the synchronized ring circuit.

The above disadvantage is eliminated in another method for triggering a pulse-frequency ultrasonic flow meter. The method is as follows. At the start of the triggering, the pulse former of the synchronized ring circuit operates in the self-oscillation mode, its natural oscillation period being selected to be somewhat greater than the maximum pulse propagation time in the synchronized ring circuit. As in the foregoing case, the former transmits a pulse to an emitting transducer whose signal is received by the receiving transducer. This signal is received before the former of the synchronized ring circuit produces a second pulse. The received pulse accounts for a forced triggering of the former, whereby the latter operates in the forced oscillation mode.

If there are disturbances in the acoustic channel, no pulses arrive from the receiving transducer. The presence of detected voltage indicates that the flow meter is back in its operating state and that one may record the measurements.

There is known an ultrasonic flow meter adapted for the aforedescribed case method and comprising two synchronized ring circuits connected to a measuring unit and an amplitude discriminator. The trigger pulse former of each synchronized ring circuit can operate in both the self-oscillation and single-shot modes. At the instant the flow meter is triggered into action, the pulse former of the synchronized ring circuit is operating in the self-oscillation mode, its natural oscillation period being selected to be somewhat greater than the maximum pulse propagation time in the synchronized ring circuit. Similarly to the aforedescribed case, the former transmits a pulse to the emitting transducer, which is received by the receiving transducer. The reception takes place before the former of the synchronized ring circuit produces a second pulse. The received pulse brings about a forced triggering of the former which operates in the forced oscillation mode. If there are disturbances in the acoustic channel, no pulses arrive from the receiving transducer, and the former operates in the self-oscillation mode. As soon as the normal working condition of the acoustic channel is re-established, the first received pulse brings about a forced triggering of the former of the synchronized ring circuit, whereby the flow meter is brought back to its operating state. In order to ascertain the correctness of measurements, the amplitude detection of the receiving transducer's output signal is carried out, and the output voltage of the amplitude detector indicates that the flow meter is in the working state.

The foregoing method is disadvantageous in that the operating condition of the flow meter cannot be assessed correctly in the presence of interference at its input.

All the aforedescribed types of flow meters have a low noise immunity both in the course of triggering and during operation. This is due to the fact that the synchronized ring circuit conducts current throughout the operation. If the former of the synchronized ring circuit is actuated by a spurious signal, two or more signals may circulate through the ring circuit, distorting the measurements.

Also known is a method for triggering an ultrasonic flow meter comprising a synchronized ring circuit, which method consists in applying trigger pulses to the synchronized ring circuit, whereby the latter is periodically turned on and off. According to the method, the information on the presence of a pulse circulating through the synchronized ring circuit is stored so as to restore the operating condition of the flow meter following a temporary disturbance in the acoustic channel. The noise immunity of the flow meter is improved by turning the synchronized ring circuit off for a period of time which is shorter than the estimated time of propagation of a signal in the electroacoustic channel.

A known ultrasonic flow meter is adapted for the foregoing triggering technique and comprises at least one synchronized ring circuit composed, in a series arrangement, of a shaping amplifier, an inhibitor, an excitation pulse former and two electroacoustical converters separated by a gap intended for passage of a medium to be subjected to flow rate measurements. The transducers are oriented with respect to each other so as to enable one of them to transmit and the other receive an acoustical signal traveling at an angle other than 90° to the direction of the flow. The flow meter further includes a trigger pulse unit and a measuring unit which are connected to the synchronized ring circuit. Finally, the flow meter incorporates a one-shot oscillator connected to the inhibitor. The trigger pulse unit is a delayed feedback oscillator (cf. USSR Inventor's Certificate No. 526,827, Cl. G01 P 5/00).

The latter flow meter operates as follows. The autocirculation pulse actuates the delayed feedback oscillator which triggers the flow meter back into action following a temporary disturbance in the acoustic channel. In order to raise the noise immunity of the flow meter, the synchronized ring circuit is turned on by the one-shot oscillator which is actuated by a pulse received by the electroacoustical transducer. This oscillator is actuated for a period of time which is shorter than the estimated time of propagation of the signal in the electroacoustical channel.

The aforedescribed method is disadvantageous in that it does not provide for automatically triggering the flow meter. Besides, an increase of the time of propagation of the signal in the medium accounts for a prolongation of the period during which the synchronized ring circuit conducts current, which means there is a possibility of the synchronized ring circuit being turned on by a spurious signal.

The flow meter under consideration cannot be triggered automatically, which is an important drawback if it is to be incorporated in an automatic flow rate control system. An increased propagation time of the signal in the acoustic channel means a longer time during which the synchronized ring circuit conducts current. The resultant possibility of the synchronized ring circuit being brought into action by a spurious signal affects the accuracy of measurements.

Besides, with low flow velocities, the difference of the frequencies in Equation (1) is quite small. Consider this example: $\alpha = 45°$, $D = 1$ m, and $V = 0.1$ m/sec; in this case, $\Delta f = 0.1$ Hz, which means that the measurement time is 10 seconds; clearly, this is too long.

The above considerations rule out the possibility of measuring instantaneous flow rates, which also affects the overall accuracy of measurements. On the whole, the flow meter under consideration does not fit into automatic control systems.

SUMMARY OF THE INVENTION

It is an object of the present invention to provide a method for triggering an ultrasonic flow meter of the type that comprises a synchronized ring circuit, which method would make the operation of the flow meter fully automatic.

It is another object of the invention to improve the noise immunity of the pulse autocirculation process in the synchronized ring circuits.

It is a further object of the invention to provide a criterion which would make it possible to ascertain that the triggering is over and the flow meter is in its operating state.

It is a further object of the invention to provide a simple, reliable, noise-proof and fast-acting ultrasonic flow meter which would be adapted for automatic triggering and which would ensure a high accuracy of measurements.

The foregoing and other objects of the present invention are attained by providing a method for triggering an ultrasonic flow meter comprising a synchronized ring circuit, which method consists in applying trigger pulses to the synchronized ring circuit and periodically turning it on and off. In the method of the invention, the synchronized ring circuit is turned on and off by trigger pulses whose repetition period is varied within the range of possible changes of the repetition period of autocirculation pulses of the synchronized ring circuit until an autocirculation pulse is matched with a trigger pulse, at which instant the application of trigger pulses to the synchronized ring circuit is discontinued by matching the frequency of the trigger pulses with that of the autocirculation pulses through the use of automatic phase control of the trigger pulse frequency, the application of trigger pulses to the synchronized ring circuit being resumed when there are no autocirculation pulses in said synchronized ring circuit.

In order to improve the noise immunity, it is expedient that the synchronized ring circuit should be turned on for periods of time which are not in excess of the trigger pulse duration. The noise immunity can also be improved by limiting the trigger pulse duration at a moment the autocirculation pulse is matched with the trigger pulse.

The triggering time can be reduced by varying the trigger pulse repetition period with a pitch not greater than the trigger pulse duration.

The accuracy of measurements can be improved by recording the moment the autocirculation pulse is matched with the trigger pulse, which moment serves to indicate that the start-up is over and that the flow meter is in operation.

The objects of the present invention are further attained by providing an ultrasonic flow meter adapted for the foregoing triggering method and comprising at least one synchronized ring circuit composed, in a series arrangement, of a shaping amplifier, an inhibitor, an excitation pulse former and two electroacoustical transducers separated from each other by a gap intended for passage of a medium whose flow rate is to be measured, which transducers are oriented in relation to each other so as to enable one transducer to transmit and other transducer to receive an acoustical signal traveling at an angle other than 90° to the flow direction, the flow meter further including a trigger pulse unit and a measuring unit, both connected to the synchronized ring circuit. In accordance with the invention, the trigger pulse unit comprises a controlled master oscillator whose output is connected to a first input of an AND gate, a first input of a storage element, a first input of a search and automatic phase control circuit and a first input of the measuring unit. An output of the controlled master oscillator is connected to an output of the search and automatic phase control circuit, whose second input is connected to an output of the storage element connected, in turn, to a second input of the AND gate. The output of the AND gate is connected to a trigger input of the shaping amplifier and a control input of the inhibitor whose output is connected to a second input of the storage element.

The objects of the present invention are also attained by providing the flow meter with a unit for checking the correctness of measurements, whose inputs are connected to the output of the storage element and that of the controlled master oscillator, respectively, whereas its output is connected to an enable input of the measuring unit.

The objects of the invention are further attained by providing the trigger pulse unit with a frequency divider interposed in series between the output of the controlled master oscillator and a common point of connection of the input of the storage element, the input of the search and automatic phase control circuit and the input of the AND gate.

The method for triggering an ultrasonic flow meter and the flow meter adapted for this method make it possible to automate flow rate measurements. The invention makes it possible to improve the noise immunity and operating speed of flow meters and to raise the accuracy of measurements.

BRIEF DESCRIPTION OF THE ACCOMPANYING DRAWINGS

Other objects and advantages of the present invention will become more apparent from a consideration of the following detailed description of preferred embodiments thereof, taken in conjunction with the accompanying drawings, wherein:

FIG. 1 is a block diagram of an embodiment of an ultrasonic flow meter of the invention;

FIG. 2 is a block diagram of the ultrasonic flow meter of FIG. 1, including a unit for checking the correctness of measurements, in accordance with the invention;

Figure 3:
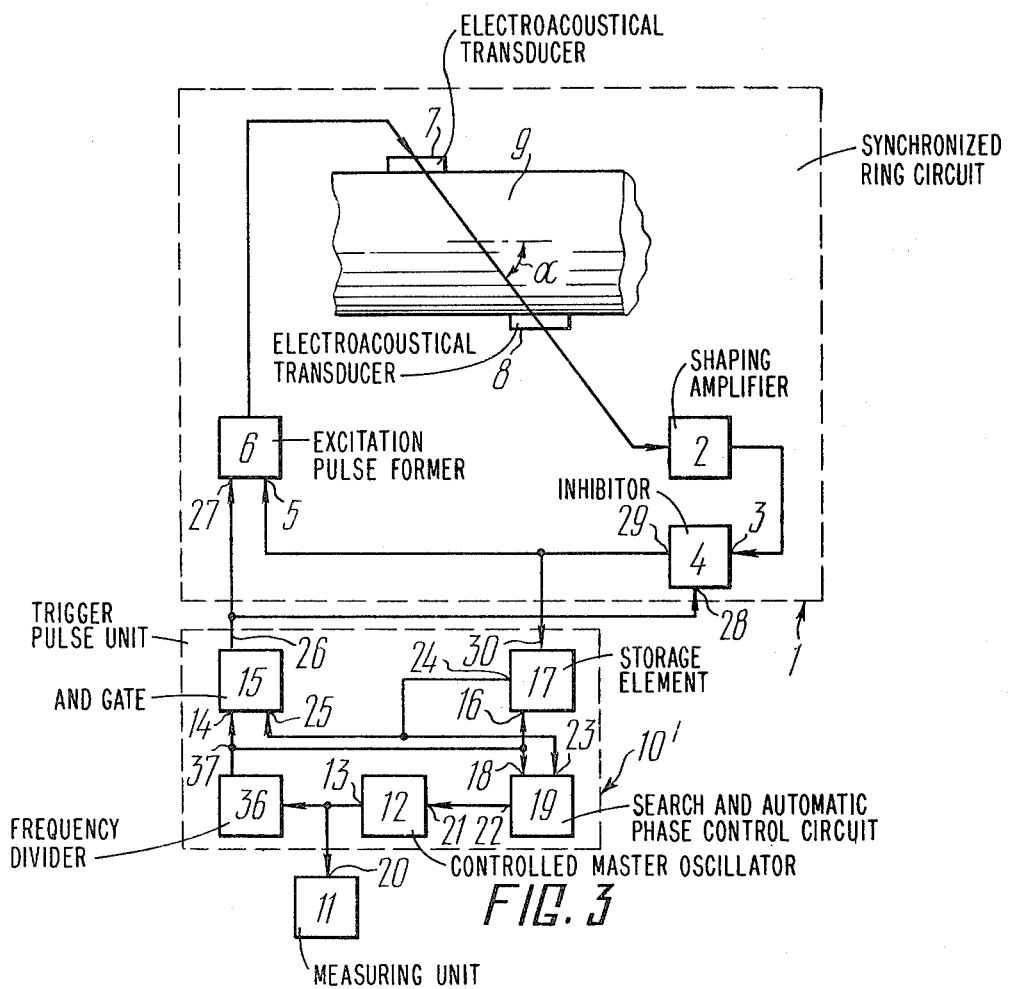
FIG. 3 is a block diagram of the ultrasonic flow meter of FIG. 1, including a frequency divider, in accordance with the invention.

FIGS. 4a, b, c, d, e are voltage diagrams which explain the operation of the flow meter of FIG. 1;

FIGS. 5a, b, c, d, e, f are voltage diagrams which explain the operation of the flow meter of FIG. 3.

DETAILED DESCRIPTION OF THE INVENTION

The method according to the invention for triggering an ultrasonic flow meter comprising a synchronized ring circuit is as follows. Trigger pulses are applied to the synchronized ring circuit, their repetition period varying within the range of possible changes of the repetition period of autocirculation pulses of the synchronized ring circuit. This means that the minimum trigger pulse period, $T_{min}$, must be less than the minimum time of propagation of a signal in the acoustic channel:

$$T_{min} < L/(C_{max} + V'_{max}), \qquad (2)$$

where

L is the distance between the electroacoustical transducers, covered by acoustical waves traversing the medium whereof the flow rate is measured;

$C_{max}$ is the maximum speed of propagation of ultrasound in the medium, which depends on the properties of the medium and external conditions;

$V'_{max}$ is the projection of the maximum possible velocity of the medium on the direction of the ultrasonic beam.

The maximum period, $T_{max}$, of trigger pulses must be greater than the maximum time of propagation of the signal in the acoustic channel:

$$T_{max} > L/C_{min} - V'_{max}, \qquad (3)$$

where $C_{min}$ is the minimum speed of propagation of ultrasound in the medium, depending on the properties of the medium and external conditions.

The pitch of the changes of the period is not to be greater than the trigger pulse duration.

The trigger pulse repetition period is varied until an autocirculation pulse coincides in time with a trigger pulse, whereupon the application of trigger pulses to the synchronized ring circuit is stopped by matching the frequency of trigger pulses with that of autocirculation pulses, which is done by means of continuous phase adjustment of the frequency of trigger pulses.

The phase adjustment goes on as long as the flow meter is in operation.

Disturbances in the acoustic channel normally lead to a disappearance of the autocirculation pulses. In such cases, phase-adjusted pulses are applied to the synchronized ring circuit. With the synchronized ring circuit in operation, it is periodically turned on and off by trigger pulses. The synchronized ring circuit may be turned on for specified periods of time. However, it is strongly recommended that it should be turned on for periods of time which are not in excess of the trigger pulse duration which should be limited at an instant an autocirculation pulse is matched with a trigger pulse.

Double-frequency circulation of pulses through the synchronized ring circuit is avoided by meeting this condition:

$$(C_{max} + V'_{max})/(C_{min} - V'_{min}) < T_{max}/T_{min} < 2 \qquad (4)$$

The foregoing may be easily complied with, keeping in mind that normally $$(C_{max}+V'_{max})/(C_{min}-V'_{min}) < 1.5 \qquad (5)$$

The flow meter according to the invention, whereof a block diagram is presented in FIG. 1, is intended for measuring the flow rates of liquid media transported through pipelines and is adapted for the method of this invention.

This flow meter comprises at least one synchronized ring circuit 1 (FIG. 1) incorporating a shaping amplifier 2 connected to an input 3 of an inhibitor 4 connected to an input 5 of an excitation pulse former 6. The flow meter further includes two electroacoustical transducers, 7 and 8, separated by a gap 9 intended for passage of a medium whose flow rate is to be measured.

The transducers 7 and 8 are arranged on the opposite sides of a pipeline and oriented in relation to each other so as to enable one of them to transmit an acoustical signal and the other to receive that signal. The acoustical signal travels at an angle $\alpha$ other than 90° to the direction of the flow through the pipeline. The ultrasonic flow meter according to the invention further includes a trigger pulse unit 10 and a measuring unit 11 which are both connected to the synchronized ring circuit 1.

The trigger pulse unit 10 comprises a controlled master oscillator 12 whose output 13 is connected to an input 14 of an AND gate 15, an input 16 of a storage element 17, an input 18 of a search and automatic phase control circuit 19 and an input 20 of the measuring unit 11. An input 21 of the controlled master oscillator 12 is connected to an output 22 of the search and automatic phase control circuit 19. An input 23 of the search and automatic phase control circuit 19 is connected to an output 24 of the storage element 17 which, in turn, is connected to an input 25 of the AND gate 15 whose output 26 is connected to a trigger input 27 of the former 6 and a control input 28 of the inhibitor 4 whose output 29 is connected to an input 30 of the storage element 17.

Unlike the embodiment of FIG. 1, the ultrasonic flow meter of FIG. 2 additionally includes a unit 31 for checking the correctness of measurements. Inputs 32 and 33 of the unit 31 are connected to the output 24 of the storage element 17 and the output 13 of the controlled master oscillator 12, respectively. An output 34 of the unit 31 for checking the correctness of measurements is connected to an enable input 35 of the measuring unit 11.

Unlike the trigger pulse unit 10 of FIG. 1, its version 10' of FIG. 3 is provided with a frequency divider 36 connected in series between the output 13 of the controlled master oscillator 12 and a common point 37 of connection of the input 16 of the storage element 17, the input 18 of the search and automatic phase control circuit 19 and the input 14 of the AND gate 15.

The function of the inhibitor 4 may be performed by an EXCEPT gate. The function of the storage element 17 may be performed by an RS flip-flop. The function of the unit 31 (FIG. 2) for checking the correctness of measurements may be performed by a D flip-flop.

The search and automatic phase control circuit 19 is a potential-accumulating element, such as a capacitor, complete with a discharger.

The triggering method of the present invention is applicable to the ultrasonic flow meter according to the invention and is carried out as follows:

From the output 22 (FIG. 1) of the search and control circuit 19, voltage is applied to the input 21 of the controlled master oscillator 12, readjusting its frequency.

At a moment supply voltages are applied, voltage across the output 22 of the search and phase control circuit 19 is zero. The pulse period of the controlled master oscillator 12 is at its minimum, i.e. $T_{min}$ (FIG. 4a), and less than the minimum time of propagation of a signal through the acoustic channel. The period of the controlled master oscillator 12 is selected so that the maximum pulse period, $T_{max}$, at its output should be greater than the maximum time of propagation of a signal through the acoustic channel. This means that the conditions of Equations (2) and (3) must be complied with.

At a moment of the arrival of supply voltages, there is no pulse at the output 13 of the controlled master oscillator and a low level is observed at said output 13. This level is stored by the storage element 17 with a high level at its output 24. In the initial state, there is a high level at the output 26 of the AND gate 15. The output 24 of the storage element 17 is connected to the input 25 of the AND gate, so the first positive pulse 38 (FIG. 4a) is applied from the output 13 of the controlled master oscillator 12 to the AND gate 15. As this takes placed, a pulse 39 (FIG. 4b) is applied to the input 28 (FIG. 1) of the inhibitor 4 and drives the latter into conduction. The pulse 39 is also applied to the input 27 of the former 6 and drives it into conduction. The former 6 is actuated by the trailing edge of the positive pulse 39 (FIG. 4b).

A pulse 40 (FIG. 4c) is applied from the former 6 (FIG. 1) to the transducer 7 to be converted to an ultrasonic signal which traverses the medium whose flow rate is to be measured. The acoustic signal is then received by the transducer 8 which converts it to an electric signal. The electric signal is applied to the shaping amplifier 2 which amplifies it and transforms it into a square pulse 41 (FIG. 4d). The pulse 41 is applied to the inhibitor 4 (FIG. 1). The pulse produced by the shaping amplifier 2 is delayed with respect to the pulse arriving from the output of the former 6 by a time t. The period of the controlled master oscillator 12 is kept at a minimum and less than t. As a result, the next pulse 42 (FIG. 4b) is applied from the output 26 of the AND gate 15 to the input 28 of the inhibitor 4 before the arrival of the pulse from the output of the shaping amplifier 2. Thus, the inhibitor 4 is cut off by the moment of arrival of the pulse from the shaping amplifier 2. Nevertheless, the pulse 42 (FIG. 4b) from the output of the AND gate 15 passes through the acoustic channel as the first pulse, etc. At the same time positive pulses are applied from the output 13 of the controlled master oscillator 12 to the input 18 of the search and automatic phase control circuit 19, whereby its output voltage is increased (FIG. 4e). The period of the controlled master oscillator 12 increases until by the time a pulse 43 (FIG. 4d) from the shaping amplifier 2 is applied to the inhibitor 4, the latter is driven into conduction by a pulse 44 (FIG. 4a) arriving from the master oscillator 12. The pulse 43 (FIG. 4d) is applied from the shaping amplifier 2 to the input 5 (FIG. 1) of the former 6 which is actuated by the leading edge of the negative pulse. The synchronizing ring circuit is turned on per a synchropulse 45 of FIG. 4c. At the same time the negative pulse is applied from the output 29 of the inhibitor 4 to the input 30 (FIG. 1) of the storage element 17. As a result, there is a low level at the output 24 of the storage element 17 and an inhibit signal is applied to the AND gate 15, whereby the duration of a pulse 46 (FIG. 4b) at the output of the AND gate 15 is reduced per a time $t_1$ (FIGS. 4a to 4e). The trailing edge of the positive pulse at the output 26 of the AND gate 15 is matched with the leading edge of the negative pulse at the output 29 of the inhibitor 4, which means that further operation of the controlled master oscillator 12 has no effect upon the synchronized ring circuit 1. The controlled master oscillator 12 is thus automatically switched off.

At this point, the search and automatic phase control circuit 19 stops operating in the search mode and starts matching the phase of the pulses produced by the master oscillator 12 with that of the autocirculation pulses of the synchronized ring circuit 1. The trailing edge of the positive pulse arriving from the controlled master oscillator 12 again establishes a high level at the output of the storage element 17. The trigger pulse from the master oscillator 12 is applied to the input 18 of the search and automatic phase control circuit 19. Pulses from the output 24 of the storage element 17 are applied to the input 23 of the circuit 19. The leading edge of these pulses is matched with that of the ring circuit pulse passed through the inhibitor 4. The search and automatic phase control circuit 19 determines the time difference between the trigger pulse and the leading edge of the autocirculation pulse of the synchronized ring circuit. The difference is converted to a control signal which is used to control the phase and frequency of the controlled master oscillator 12. These parameters are controlled so that the leading edge of the autocirculation pulse of the synchronized ring circuit should be found within the trigger pulse, preferably, in its middle. Thus the leading edge of the trigger pulse actuates the inhibitor 4 and the synchronized ring circuit. On the other hand, the inhibitor 4 and ring circuit 1 are cut off by the leading edge of the autocirculation pulse. Thus, the time during which the synchronized ring circuit conducts current amounts to half the trigger pulse duration. From the viewpoint of noise immunity, the duration of the trigger pulse should be 1 to 2 per cent of the autocirculation pulse repetition period.

Thus, the output pulses of the controlled master oscillator 12 are related in phase and frequency to the pulses of the synchronized ring circuit. The repetition frequency of the synchronized ring circuit pulses can be determined by applying pulses from the output of the controlled master oscillator 12 to the input 20 of the measuring unit 11.

In case of a disturbance in the acoustic channel, output pulses of the controlled master oscillator 12 continue to arrive at the input of the search and automatic phase control circuit 19, increasing voltage at its output. This is accompanied by an increase of the trigger pulse period.

This period is at its maximum with a maximum voltage at the output of the search and automatic phase control circuit 19. A discharge follows to reduce that voltage to zero, whereupon the flow meter operates as hereinbefore described.

The ultrasonic flow meter of FIG. 2 is similar to that of FIG. 1, but operates to permit the checking of the correctness of measurements. The idea is to find out if each pulse of the synchronized ring circuit 1 is matched with the trigger pulse. For this purpose, pulses are applied from the output 24 of the storage element 17 to the information input 32 of the unit 31 for checking the correctness of measurements. The unit 31 is also referred to as the storage element 31. Meanwhile, pulses are aplied from the output 13 of the controlled master oscillator 12 to the input 33 of the storage element 31, which is a synchroinput. The present of voltage at the output 34 of the storage element 31 indicates that the flow meter is in good working condition. This voltage is applied to the enable input 35 of the measuring unit 11.

In case of a disturbance in the acoustic channel, i.e., the gap 9 filled with the medium whose flow rate is being measured, a high level is observed at the information input 32 of the storage element 31 at the time of arrival of the trailing edge of the pulse applied from the controlled master oscillator 12 to the input 33 of the storage element 31. The high level indicates that the synchronized ring conduit 1 is off. The trailing edge of the trigger pulse erases the information on the matching of the trigger pulses and those of the synchronized ring circuit. An inhibit signal is applied from the output 34 of the storage element 31 to the enable input 35 of the measuring unit 11. From the output 13 of the controlled master oscillator 12, pulses continue to arrive at the input 18 of the search and automatic phase control circuit 19, increasing the voltage at its output 22. As this takes place, the trigger pulse period increases. When the voltage at the output 22 of the search and automatic phase control circuit 19 reaches a maximum, a discharge follows to reduce that voltage to zero, whereupon the flow meter operates as hereinbefore described.

To actuate the flow meter during the very first cycle of variation of the trigger pulse period, it is necessary that each next trigger pulse period should be changed by not more than the trigger pulse duration.

The only difference between the ultrasonic flow meter of FIG. 3 and that of FIG. 1 is that the former includes the frequency divider 36 incorporated in the triggering unit 10'. The divider 36 makes it possible to divide the frequency of pulses (FIG. 5a) at the output of the controlled master oscillator 12 (FIG. 3) by K. The output pulses of the master oscillator 12 are related in phase and frequency to the pulses of the synchronized ring circuit 1, but the frequency of the former pulses is K times higher than that of the latter pulses.

If a flow meter according to the invention comprises two synchronized ring circuits, the measuring unit will find the following difference $\Delta F$ between the frequencies of the controlled master oscillators:

$$F = \text{Sin } 2\alpha / D \cdot V \cdot K \qquad (6)$$

With K = 100, the measurement time is 0.1 sec. Thus, the flow meter of FIG. 3 is fit for instantaneous flow rate measurements and for actual operation as part of an automatic control system.

The voltage diagrams of FIGS. 5b, c, d, e and f, which illustrate the operation of the ultrasonic flow meter of FIG. 3, are similar to the voltage diagrams of FIGS. 4a, b, c, d, e. The only difference is that FIG. 5b, which corresponds to FIG. 4a, shows a train of pulses at the output of the frequency divider 36.

What is claimed is:

1. A method for triggering an ultrasonic flow meter having a synchronized ring circuit, said method comprising the steps of
    applying a train of trigger pulses to said synchronized ring circuit;
    periodically turning said synchronized ring circuit on and off by said trigger pulses;
    varying the repetition period of said trigger pulses within the range of possible changes of the repetition period of autocirculation pulses of said synchronized ring circuit until an autocirculation pulse is matched with a trigger pulse;

discontinuing the application of said trigger pulses to said synchronized ring circuit at the moment an autocirculation pulse is matched with a trigger pulse, by continuous automatic phase control to match the frequency of the trigger pulses with that of the autocirculation pulses; and resuming the application of said trigger pulses to said synchronized ring circuit as soon as there are no autocirculation pulses in said synchronized ring circuit.

2. A method as claimed in claim 1, wherein said synchronized ring circuit is turned on for periods of time which are not in excess of the trigger pulse duration.

3. A method as claimed in claim 2, wherein the trigger pulse duration is limited at the instant an autocirculation pulse of the synchronized ring circuit is matched with a trigger pulse.

4. A method as claimed in claim 1, wherein the trigger pulse repetition period is varied with a pitch which is not greater than the trigger pulse duration.

5. A method as claimed in claim 1, wherein the moment an autocirculation pulse of the synchronized ring circuit is matched with a trigger pulse is recorded and serves to indicate that the triggering is over and that the ultrasonic flow meter is in operation.

6. An ultrasonic flow meter, comprising
at least one synchronized ring circuit;
a shaping amplifier in said synchronized ring circuit, said shaping amplifier having an input and an output;
an inhibitor in said ring circuit, said inhibitor having a first input connected to the output of said shaping amplifier, a second input and an output;
an excitation pulse former in said ring circuit, said excitation pulse former having a first input connected to the output of said inhibitor, a second input and an output;
a first electroacoustical transducer electrically connected to the output of said excitation pulse former;
a second electroacoustical transducer electrically connected to the input of said shaping amplifier, said first and second electroacoustical transducers having a gap therebetween intended for passage of a medium whose flow rate is to be measured, said electroacoustical transducers being oriented in relation to each other so that one of them is capable of transmitting and the other is capable of receiving an acoustical signal traveling at an angle other than 90° to the flow direction;
an AND gate having a first input, a second input and an output connected to the second input of said excitation pulse former;
a storage element having a first input connected to the output of said inhibitor, a second input and an output connected to the first input of said AND gate;
a search and automatic phase control circuit having a first input connected to the output of said storage element, a second input and an output;
a controlled master oscillator having an input connected to the output of said search and automatic phase control circuit and an output connected to the second input of said AND gate, to the second input of said storage element and to the second input of said search and automatic phase control circuit; and
a measuring unit having an input connected to the output of said controlled master oscillator.

7. An ultrasonic flow meter as claimed in claim 6, wherein said measuring unit has a second input, and further comprising a unit for checking the correctness of measurements, said checking unit having a first input connected to the output of said storage element, a second input connected to the output of said controlled master oscillator and an output connected to the second input of said measuring unit.

8. An ultrasonic flow meter as claimed in claim 7, further comprising a frequency divider connected in series between the output of said controlled master oscillator and a common point of connection of the second input of said AND gate, the second input of said storage element and the second input of said search and automatic phase control circuit.

9. An ultrasonic flow meter as claimed in claim 6, further comprising a frequency divider connected in series between the output of said controlled master oscillator and a common point of connection of the second input of said AND gate, the second input of said storage element and the second input of said search and automatic phase control circuit.

* * * * *